United States Patent [19]

Wolfangel

[11] 4,062,933

[45] Dec. 13, 1977

[54] COLLOIDAL COMPOSITIONS WITH PROTECTIVE AGENTS SUITABLE FOR RADIOACTIVE LABELING

[75] Inventor: Robert G. Wolfangel, Ballwin, Mo.

[73] Assignee: Mallinckrodt, Inc., St. Louis, Mo.

[21] Appl. No.: 581,314

[22] Filed: May 27, 1975

[51] Int. Cl.$^2$ .................. A61K 43/00; A61K 29/00; B01J 13/00

[52] U.S. Cl. .................. 424/1; 252/313 R

[58] Field of Search ............ 424/1; 252/313 R, 363.5; 250/303

[56] References Cited

U.S. PATENT DOCUMENTS

| | | | |
|---|---|---|---|
| 3,674,900 | 7/1972 | Thompson | 424/1 |
| 3,683,066 | 8/1972 | Ascanio et al. | 424/1 |
| 3,810,976 | 5/1974 | Ficken et al. | 424/1 |

OTHER PUBLICATIONS

Eckelman et al, Journal of Nuclear Medicine, vol. 12, No. 11, 1971, pp. 707-710.

Lin et al, Journal of Nuclear Medicine, vol. 13, No. 1, 1972, pp. 58-65.

Deutsch et al, Radiopharmaceuticals and Labelled Compounds, vol. 1, International Atomic Energy Agency, Vienna, 1973, pp. 189-194.

*Primary Examiner*—Benjamin R. Padgett
*Assistant Examiner*—Christine M. Nucker
*Attorney, Agent, or Firm*—Roy J. Klostermann

[57] ABSTRACT

An improved process for lyophilizing pharmaceutical products capable of being labelled with a radionuclide.

28 Claims, No Drawings

4,062,933

COLLOIDAL COMPOSITIONS WITH PROTECTIVE AGENTS SUITABLE FOR RADIOACTIVE LABELING

BACKGROUND OF THE INVENTION

1. Field of the Invention

This invention is directed to methods for preparing lyophilized products suitable for labelling or tagging with a radionuclide, to the radio labelled products themselves and to their use as diagnostic scanning agents. More particularly this invention is directed to lyophilizing a dispersion suitable for radionuclide labelling which contains a protective agent.

2. Description of the Prior Art

Currently there are numerous radiopharmaceutical products useful as diagnostic scanning agents especially, Tc-99m-labelled products. Generally these pharmaceutical products which are usually dispersions of minute particles are radiolabelled shortly before use. Such dispersions must be maintained in a suitable form so they can be labelled and used.

A number of ways are available in the art to keep these dispersions in such a form, namely, freezing or lyophilizing. Of these, lyophilizing is preferred. However, the physical and chemical properties of lyophilized dispersions normally degrade during lyophilization or before radiolabelling which may be 6 to 9 months later. This, of course, is undesirable.

Consequently an improved freeze drying or lyophilization process would be an advancement in the art.

BRIEF DESCRIPTION OF THE INVENTION

Surprisingly, in accordance with this invention there is provided an improvement in a process wherein a dispersion of particles suitable for radioactive labelling and use as a diagnostic scanning agent is prepared and lyophilized and where the physical and chemical properties of said particles degrade during lyophilization or thereafter, which involves additionally including in said dispersion a protective agent.

These protective agents reduce the degradation of the physical and chemical properties, particularly those of particle size and radionuclide affinity, of the dispersion during lyophilization and normal storage or aging prior to labelling. On labelling, these dispersions are suitable as diagnostic scanning agents.

Another aspect of this invention is directed to the products prepared by the aforementioned process as well as the radiolabelled products prepared by the aforementioned process.

Another aspect of this invention is directed to a method for using the aforementioned radiolabelled products as scanning agents.

DETAILED DESCRIPTION OF THE INVENTION

The protective agents that may be used in the process of this invention include any pharmaceutically acceptable material other than serum albumin that will effectively reduce degradation during lyophilization of the dispersed particles and aging or storage thereafter. These include carbohydrates, organic aids, amino acids, alcohols or mixtures thereof.

Illustrative carbohydrates include sugars such as monosaccharides and disaccharides and non-sugars illustrated by polysaccharides. Monosaccharides are those sugars containing 3 or more carbon atoms that cannot be split up any further by hydrolysis. Disaccharides are those sugars that split up under the influence of hydrolysis into two molecules of monosaccharides. The polysaccharides include those sugars which upon hydrolysis yield 3, 4 or more monosaccharides and a large number of related substances which bear a close chemical relationship to sugars since by hydrolytic change they can be converted into many molecules of glucose or other monosaccharides.

Specific examples of monosaccharides include trioses, tetroses, pentoses, hexoses. More specific example include glycerose, erythrose, threose, arabinose, xylose, ribose, lyxase, dextrose, levulose, sorbose, galactose, mannose, etc. Specific examples of disaccharides include sucrose, lactose, maltose, isomaltose, trehalose, cellobiose, gentiobiose, melibiose, glucoxylose, primeverose, vicianose, etc.

Classes of polysaccharides include trisaccharides, tetrasaccharides, starches, gums, celluloses, etc. Specific examples include reaffinose, gentianose, melezitose, stachyose, dextrins, insulin, glycogen, galactosan, mannosan, natural gums, pentosans, mucilages, and pectin compounds.

Preferred sugars include dextrose and lactose.

Other examples of carbohydrates may be found in *Remington's Practice of Pharmacy,* Eleventh Edition, pages 1019–1032, which is incorporated herein by reference.

All pharmaceutically accepted organic acids sand salts thereof may be used in the practice of this invention. Monocarboxylic acids are charcterized by the formula RCOOH where R is an aliphatic, alicyclic, or aromatic group. Aliphatic acids include those containing 1 to 30, preferably 1 to 10, carbon atoms such as formic, acetic, propionic, butyric, valeric, sorbic, caproic, enanthic, caprylic, pelargonic, capric, lauric, myristic, palmitic, and stearic acids. Branched chain organic acids may also be employed such as isobutyric acid or isolauric acid. Dicarboxylic acids, containing up to 20, preferably 2 to 10, carbon atoms, may also be employed, for example, oxalic acid, malonic acid, succinic acid, glutaric acid, adipic acid, pimelic acid, suberic acid, azelaic acid, sebacic acids, etc. Tricarboxylic acids containing up to 20 carbon atoms, preferably 3 to 10 carbon atoms, may be used such as citric acid.

It is preferred to use citric, ascorbic, succinic or glutaric acid.

Amino acids that may be used include aliphatic amino acids, aromatic amino acids, sulfur containing amino acids, heterocyclic amino acids, etc. Specific examples include glycine, alanine, serine, threonine, valine, leucine, isoleucine, phenylalanine, tyrosine, cysteine, cystine, methionine, tryptophan, proline, hydroxyproline, aspartic acid, glutamic acid, histidine, lysine, arginine, etc. Glycine is preferred.

Other examples may be found in *Remington's Practice of Pharmacy,* Eleventh Edition, Pages 929 to 939 which is incorporated herein by reference.

All pharmaceutically accepted aliphatic or aromatic mono or poly alcohols containing 6 or more carbon atoms, preferably 6 to 12, may also be used. These include sorbitol, mannitol, etc.

Polyvinylpyrrolidone may also be used.

The method of this invention may be advantageously used with any dispersion of minute particles suitable for radioactive labelling and use as a diagnostic scanning agent which are well known to those skilled in the art. It is preferably used with denatured albumin aggregates and with stannous sulfur colloids both of which are labelled with technetium-99m. An example of a denatured macroprotein is described in U.S. Pat. No. 3,863,004 which is incorporated herein by reference. The corresponding German analog of this application was published in October, 1973. Basically, this patent describes a composition suitable for tagging with technetium-99m which consists essentially of an injectable suspension or dispersion in a buffer solution of particles of a denatured macroprotein having divalent tin bound thereto.

The practice of this invention is also applicable to dispersions comprising particles of stannous sulfur colloid dispersed in an aqueous buffer solution. A description for preparing such dispersions is described in my copending patent application entitled Radiopharmaceutical Scanning Agents filed concurrently herewith and identified as Ser. No. 581,315, said application being incorporated herein be reference.

The amount of protective agent used in this practice of this invention can be readily determined by those skilled in the art. It will depend upon the particular dispersion but it will be an amount effective to reduce the degradation of the physical and chemical properties of the dispersion during lyophilization and normal storage thereafter. Usually this is an amount of from 1 to 600 times by weight of the dispersion, preferably 1 to 400 times. For example in the case of organic acids such as citric acid and succinic acid, an amount of about 2 times to about 30 times the amount by weight of the macroaggregates of albumin is used and in the case of stannous sulfur colloid an amount of from about 1 time to about 400 times the amount by weight of the stannous sulfur colloid is used.

In the case of carbohydrates such as lactose an amount of about 2 times to about 30 times the amount by weight of the macroaggregates of albumin or 2 times to 100 times the weight of the dispersion stannous sulfur colloidal particles is used.

In the case of amino acids such as glycine an amount of about 2 times to 100 times the amount by weight of the macroaggregates of albumin or 1 time to 400 times the weight of the dispersion of stannous sulfur colloidal particles is used.

It is particularly preferable to use a combination of polycarboxylic acid and a disaccharide. Usually the polycarboxylic acid is present in an amount of from about 1 time to about 50 times and the disaccharide is present in an amount of from about 1 time to about 100 times the weight of the dispersion. In the case of macroaggregates of albumin the polycarboxylic acid is used in an amount of 1 times to 20 times the weight of the macroaggregates and the disaccharide is used in an amount of 1 times to 100 times the weight of the macroaggregates.

The lyophilized products of this invention can be conveniently reconstituted by adding normal saline solution. Alternatively, they may be reconstituted and labelled at the same time by adding a radioactive tracer. For example, technetium-99m in normal saline solution may be added directly to the product. Generators suitable for such labelling are commercially available, for example, one such generator is described in Shumate U.S. Pat. No. 3,535,085 dated Oct. 29, 1970. When the eluate and the lyophilized product are mixed binding of the technetium to the protein occurs spontaneously and quickly with an efficiency of 95% or more.

Preferably, about 30 minutes is allowed to optimize the specific activity of the tagged suspension. The mechanism of tagging is not clear but it involves oxidation of the stannous divalent ion to the tetravalent state with concurrent reduction of the heptavalent technetium to a lower oxidation state. Tetravalent tin remains attached to the protein. Within minutes of the addition of the technetium eluate thereto, the suspension of tagged albumin may be intravenously injected directly into animals or humans without any further treatment.

The effectiveness of lung scanning is optimized by using sufficient eluate to provide a tagged suspension having a specific activity of up to approximately 50 mCi Tc/mg of the macroaggregated albumin. Normally the mean particle size is from 15 to 30 microns. Five minutes after injection, the lungs of a subject contain 80% or more of the injected technetium-99m. The presence or absence of a pathological condition is then determined by radioscanning the lungs of the patient and comparing the emission pattern thereof with a standard pattern. The tagged denatured albumin is eliminated from the subject's lungs at a rate corresponding to a biological half life of approximately 3 – 15 hours.

The stannous sulfur colloid may be tagged in a similar manner.

The followimg examples illustrate the invention. All parts are by weight unless otherwise stated.

EXAMPLES

EXAMPLE 1

50 ml of normal human serum albumin (25% w/v) was added to 950 ml of sterile pyrogen free water in a 1 liter serum vial containing a stirrer and heated to about 83° for 30 minutes to denature the protein. The solution was then transferred to a cold water bath and when the temperature had reached 21° – 24° C., 10 ml of 0.415 N HCl was slowly added over a period of 10 – 12 minutes with rapid stirring. The pH of the resulting suspension was 5 – 6. The suspension was reheated to 83° C. for 9 – 11 minutes with slow stirring, causing the precipitated albumin aggregates to become more compact and less subject to fragmentation.

The reaction vial is transferred to a cool bath and 30 ml of 2M sodium acetate and 15 ml of stannous chloride were added with constant stirring. The mixture was allowed to incubate for 24 hours. After the incubation was complete, the mixture was divided equally into 250 ml SPF vials, the protein macroaggregates were washed three times by centrifugation, with resuspension in fresh acetate buffer following each washing. Following the last washing sufficient buffer was added to bring the concentration to 10 mg/ml. Sufficient lactose and succinic acid dissolved in solution were added to reduce the protein concentration to 2 mg/ml and so 24 mg/ml of succinic acid and 80 mg/ml of lactose are present.

Once this has been completed, 1 ml of the dispersion was dispensed into individual SPF vials which were quick frozen at −60° C. The vials were placed in the sublimator and when the dispersion temperature reached −30° C. and the condenser temperature −50° C. the chamber was evacuated. When the chamber atmosphere reaches 30$\mu$, the controlled shelf heat was turned on to 70° F. The vacuum was maintained for at least 32 hours and the temperature of 70° F. for at least 22 hours.

The resulting dried product retained all the desirable physical and chemical properties especially particulate size and pertechnetate affinity for periods of 6 to 12 months or longer.

EXAMPLE 2

Example 1 was repeated except glutaric acid was used in place of succinic acid.

EXAMPLE 3

Example 1 was repeated except lactose was used in place of dextrose.

EXAMPLE 4

Example 1 was repeated except 16 mg of succinic acid and 40 mg of lactose was used.

EXAMPLE 5

Example 1 was repeated except 12 mg of glutaric acid and 40 mg of lactose was used.

EXAMPLE 6

Individual vials containing 0.5 ml of a dispersion of stannous sulfur colloid were placed in a lyophilizer and then lyophilized at 50° F. shelf heating, and −4° C. product temperature control until the final product temperature reaches 0° C. (total time about 16 hours final product moisture content is 0.3–0.6 mg Karl Fisher method).

From a consideration of the above specification, it will be understood that many improvements and modifications in the details may be made without departing from the spirit and scope of the invention. It is to be understood, therefore, that the invention is not limited except as defined by the appended claims.

What is claimed is:

1. In a process wherein a dispersion of colloidal sulfur particles to which stannous ions are attached suitable for radioactive labeling and use a diagnostic agent is prepared and lyophilized and where the physical and chemical properties of said particles degrade during lyophilization or aging thereafter, the improvement comprising additionally including in said dispersion in a sufficient amount an amino acid as a protective agent to reduce degradation of the physical and chemical properties of the dispersion during lyophilization and aging thereafter.

2. A process according to claim 1 wherein said amino acid is an aliphatic amino acid.

3. A process according to claim 2 wherein said amino acid is glycine.

4. A lyophilized product prepared by the process of claim 1.

5. A lyophilized product prepared by the process of claim 2.

6. A lyophilized product prepared by the process of claim 3.

7. An injectable radiopharmaceutical scanning agent prepared by radioactively labeling a product prepared by the process of claim 1.

8. An injectable radiopharmaceutical scanning agent prepared by radioactively labeling the product prepared by the process of claim 2.

9. An injectable radiopharmaceutical scanning agent prepared by radioactively labeling the product prepared by the process of claim 3.

10. In a process wherein a radiopharmaceutical scanning agent is injected and thereafter a scan made the improvement comprising utilizing as the scanning agent the agent of claim 7.

11. In a process wherein a radiopharmaceutical scanning agent is injected and thereafter a scan made the improvement comprising utilizing as a scanning agent the agent of claim 8.

12. In a process wherein a radiopharmaceutical scanning agent is injected and thereafter a scan made the improvement comprising utilizing as a scanning agent the agent of claim 9.

13. In a process wherein a dispersion of denatured aggregates of serum albumin to which tin is attached, suitable for radioactive labeling and use as a diagnostic agent is prepared and lyophilized and where the physical and chemical properties of said particles degrade during lyophilization or aging thereafter the improvement comprising additionally including in a sufficient amount in said dispersion as a protective agent a mixture of a polycarboxylic acid and a disaccharide or monosaccharide.

14. A process according to claim 13 wherein said protective agent is a mixture of a dicarboxylic acid containing 2 to 10 carbon atoms and a disaccharide.

15. A process according to claim 13 wherein said protective agent is a mixture of (1) lactose or dextrose and (2) succinic or glutaric acid.

16. A lyophilized product prepared by the process of claim 13.

17. A lyophilized product prepared by the process of claim 14.

18. A lyophilized product prepared by the process of claim 15.

19. An injectable radiopharmaceutical scanning agent prepared by radioactively labeling a product prepared by the process of claim 13.

20. An injectable radiopharmaceutical scanning agent prepared by radioactively labeling a product prepared by the process of claim 14.

21. An injectable radiopharmaceutical scanning agent prepared by radioactively labeling a product pepared by the process of claim 15.

22. In a process wherein a radiopharmaceutical scanning agent is injected and thereafter a scan made, the improvement comprising utilizing as a scanning agent the agent of claim 19.

23. In a process wherein a radiopharmaceutical scanning agent is injected and thereafter a scan made the improvement comprising ultilizing as the scanning agent the agent of claim 20.

24. In a process wherein a radiopharmaceutical scanning agent is injected and thereafter a scan made the improvement comprising utilizing as the scanning agent the agent of claim 21.

25. In a process wherein a dispersion of colloidal particles suitable for radioactive labeling and use as a diagnostic agent is prepared by (a) forming a dispersion containing a sulfur colloid by reacting in an aqueous medium a thiosulfate with a pharmaceutically acceptable acid (b) interacting a pharmaceutically acceptable stannous salt with the dispersion of (a), thereafter buffering the resulting dispersion, and (c) lyophilizing said dispersion and where the physical and chemical properties degrade during lyophilization or aging thereafter, the improvement comprising additionally including in said dispersion in a sufficient amount an amino acid as a protective agent to reduce degradation of the physical and chemical properties of the dispersion during lyophilization and aging thereafter.

26. A lyophilized product prepared by the process of claim 25.

27. An injectable radiopharmaceutical scanning agent prepared by radioactively labelling a product prepared the process of claim 25.

28. In a process wherein a radiopharmaceutical scanning agent is injected and thereafter a scan made the improvement comprising utilizing as the scanning agent the agent of claim 27.

* * * * *